United States Patent [19]
Fuisz et al.

[11] Patent Number: 5,965,162
[45] Date of Patent: *Oct. 12, 1999

[54] PROCESS FOR FORMING CHEWABLE QUICKLY DISPERSING MULTI-VITAMIN PREPARATION AND PRODUCT THEREFROM

[75] Inventors: Richard C. Fuisz, McLean; Subraman R. Cherukuri, Vienna, both of Va.; Suresh B. Kota, Cupertino, Calif.; James L. Stewart, Arlington, Va.

[73] Assignee: Fuisz Technologies Ltd., Chantilly, Va.

[*] Notice: This patent is subject to a terminal disclaimer.

[21] Appl. No.: 09/100,531

[22] Filed: Jun. 19, 1998

Related U.S. Application Data

[63] Continuation-in-part of application No. 09/097,999, Jun. 16, 1998, which is a continuation-in-part of application No. 08/259,258, Jun. 14, 1994, which is a continuation-in-part of application No. 08/133,669, Oct. 7, 1993, Pat. No. 5,597,416, and a continuation-in-part of application No. 08/119,974, Sep. 10, 1993, Pat. No. 5,518,551.

[51] Int. Cl.[6] .............................. A61K 9/20; A61K 9/28; A61K 9/68; A61K 9/36
[52] U.S. Cl. ..................... 424/464; 424/441; 424/465; 424/466; 424/479; 424/484; 424/489
[58] Field of Search ................... 424/400, 440, 424/441, 464, 465, 466, 479, 484, 489

[56] References Cited

U.S. PATENT DOCUMENTS

| | | | |
|---|---|---|---|
| 4,873,085 | 10/1989 | Fuisz | 424/400 |
| 4,997,856 | 3/1991 | Fuisz | 514/777 |
| 5,034,421 | 7/1991 | Fuisz | 514/772 |
| 5,096,492 | 3/1992 | Fuisz | 106/215 |
| 5,279,849 | 1/1994 | Fuisz et al. | 426/658 |
| 5,380,473 | 1/1995 | Bogue et al. | 264/11 |
| 5,387,431 | 2/1995 | Fuisz | 426/658 |
| 5,427,811 | 6/1995 | Fuisz et al. | 426/465 |
| 5,518,551 | 5/1996 | Battist et al. | 127/58 |
| 5,587,172 | 12/1996 | Cherukuri et al. | 424/401 |
| 5,597,416 | 1/1997 | Fuisz et al. | 127/30 |
| 5,622,719 | 4/1997 | Myers et al. | 424/488 |
| 5,654,003 | 8/1997 | Fuisz et al. | 424/469 |
| 5,834,033 | 11/1998 | Abdi et al. | 425/8 |

OTHER PUBLICATIONS

U.S. application No. 08/259,258, Cherukuri et al., filed Jun. 14, 1998.

*Primary Examiner*—Thurman K. Page
*Assistant Examiner*—S. Howard
*Attorney, Agent, or Firm*—John F. Levis

[57] ABSTRACT

A composition and method for preparing multi-vitamin comestible units which disperse quickly in the mouth, especially when chewed, includes initiating crystallization of shearform matrix with crystallization/binding promoter and combining with an additive to form flowable, compactible micro-particulates. The combination is then shaped to form a comestible unit having high structural integrity, good appearance, and excellent release characteristics.

19 Claims, 2 Drawing Sheets

PROCESS FOR FORMING CHEWABLE QUICKLY DISPERSING MULTI-VITAMIN PREPARATION AND PRODUCT THEREFROM

RELATED APPLICATIONS

This application is a continuation-in-part of U.S. application Ser. No. 09/097,999, filed Jun. 16, 1998 which was a continuation in part of U.S. application Ser. No. 08/259,258, filed Jun. 14, 1994, which was a continuation-in-part application of U.S. application Ser. No. 08/133,669 filed Oct. 7, 1993, now U.S. Pat. No. 5,597,416 and a continuation-in-part of U.S. application Ser. No. 08/119,974 filed Sep. 10, 1993, now U.S. Pat. No. 5,518,551. Reference is also made to commonly-owned U.S. Pat. No. 5,622,719 entitled "Process And Apparatus For Making Rapidly Dissolving Dosage Units And Product Therefrom." The contents of these are incorporated herein.

BACKGROUND OF THE INVENTION

The present invention relates to the art of making chewable comestible dosage units, such as tablets, which disintegrate quickly in the mouth.

Dosage units in the form of tablets are usually prepared by compressing a formulation containing a medicinal substance or drug and other ingredients, such as excipients selected for properties which facilitate production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

Wet granulation is an expensive process because it requires many processing steps and involves considerable material handling equipment. Consequently, the process requires both energy and substantial space which should be environmentally controlled.

Generally, free water and heat are inimical to active ingredient. Wet granulation procedures involve water and/or heat. Therefore, it is desirable to provide a method for making tablets in the substantial absence of heat and free water in order to enhance the survival of active ingredients incorporated in the tablet.

Dry granulation refers to the granulation of a powder mixture by compression without the use of heat and solvent. Dry granulation is used when wet granulation is not available because the drug is sensitive to moisture or heat.

Dry granulation has many disadvantages. It requires a specialized heavy-duty tablet press to form the slug; it does not permit uniform color distribution as can be achieved with wet granulation, where dye can be incorporated into the binder liquid; the pressure roll press cannot be used with insoluble drugs because this may retard the dissolution rate; and the process tends to create dust thereby increasing the potential for cross-contamination.

Direct compression tableting has the least amount of steps. Direct compression is used in a process by which tablets are compressed directly from powder blends of the active ingredient and suitable excipients (including fillers, disintegrants, and lubricants).

Direct compression also has many technological limitations. These limitations include primarily obtaining sufficient flow, and obtaining bonding of particles to form a strong compressed tablet. Low-dose drugs are difficult to blend, that is, uniform distribution of the drug is not easily attained and unblending sometimes occurs during the compression stage. High-dose drugs do not lend themselves to direct compression because of poor flowability and poor compressibility. A typical example would be some of the antacid drugs, such as aluminum hydroxide and magnesium carbonate.

A disadvantage of all prior art processes is the production of fines usually associated with making compression tablets. In the prior art, preparation of particles for formulation of tablets by compression results in a noticeable amount of fines, i.e., very tiny particles on the order of 150 microns and less. These fines can interfere with operation of apparatus for feeding tableting machines as well as the operation of the tableting machines. This adds to the cost of production of the tablets.

Technology has been developed by the common owner of the present application and U.S. Pat. No. 5,654,003. The patent discloses a unique procedure in which compression tableting can be simply and accurately manufactured by "fuse and compression" steps. Fusion is achieved by flash flow processing, the tablet ingredients to provide shearform matrix masses which are subsequently compressed to form comestible compression units. This process includes advantages of wet and dry granulation and direct compression but does not have the disadvantages associated with these prior art procedures.

In commonly-owned patent U.S. Pat. No. 5,622,719, a rapidly-dissolving unit dosage and preparation and apparatus for making same are disclosed. The method disclosed therein includes mixing uncured shearform matrix material with an additive followed by lightly compressing the resulting mixture to form a dosage unit. The formed unit is subsequently cured by exposing to controlled ambient heat, moisture, and pressure.

Applicants' assignee also has several patents which relate to other unique delivery means. U.S. Pat. No. 4,855,326 discloses a fiber form of medicament-bearing product which can be compacted to form a sheet-like body. However, the compact body cannot be squeezed too much for fear of breaking the fibrous mass.

In U.S. Pat. No. 4,997,856, a wafer-like structure is disclosed in which a medicament is distributed on or through spun fibers which are then chopped by passing through a conventional "food grinder" (Hobart hamburger grinder). The enclosed volume of the end product is less than 30%, and preferably less than 15%, of the as-spun volume of floss.

The use of compacted spun fibers is also disclosed in U.S. Pat. Nos. 5,034,421 and 5,096,492.

While the procedure described in U.S. Pat. No. 5,622,719 discloses a technique for making a rapidly dissolving dosage unit, none of the other procedures provide a technique for forming a dosage unit which quickly disintegrates in the mouth of the consumer, but which can be conveniently manufactured for shipment and sales.

SUMMARY OF THE INVENTION

The present invention deals with compositions and methods for preparing comestible units which quickly disperse in the mouth of the consumer, especially when chewed, and the units themselves. The method includes initiating crystallization of shearform matrix before combining the shearform matrix with an additive to form flowable, compactible micro-particulates. The combination, which includes at least partially crystallized shearform matrix, is then compacted to form the comestible unit.

In one preferred form of the invention, the active ingredient is a multi-vitamin preparation and the crystallization/binding promoter is ethanol. Other preferred actives can include edible calcium salts for antacid and mineral supplements.

One manifestation of the present invention is a method of administering an active ingredient to a human host. The method includes ingesting a quick dissolve comestible unit prepared by the method of the present invention. The next step requires the host to retain the quick dissolve unit in the oral cavity for a time sufficient to contact the unit with saliva while in the oral cavity. Finally, the human host can introduce water to the oral cavity, while the unit is retained therein, to enhance dissolution of the dosage unit.

Other embodiments of the invention involve chewable comestible units. These units, which are preferably tablets, are specially formulated and processed so that they are easily chewable and readily soluble when chewed. Water can be used to enhance dispersion/dissolution after ingestion.

Moreover, the dispersability of the unit is perceived as nearly instantaneous when chewed. Consequently, the consumer does not sense the effects of unpleasant ingredients lingering in the oral cavity.

Tablets containing multivitamins can be made which are pleasant tasting, have no gritty taste or mouthfeel, and dissolve quickly. In addition, they can be made chewable, while retaining the friability of tablets. Formulating a particularly palatable multi-vitamin chewable preparation is unusually challenging because of the mix of many water-soluble and insoluble active vitamin preparations included in one tablet.

It is, therefore, an object of the invention to provide another method for preparing a chewable dosage unit which quickly disintegrates in the mouth.

These and other advantages and objects of the present invention will be appreciated from the following description. The description and the examples are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

Figure 1:
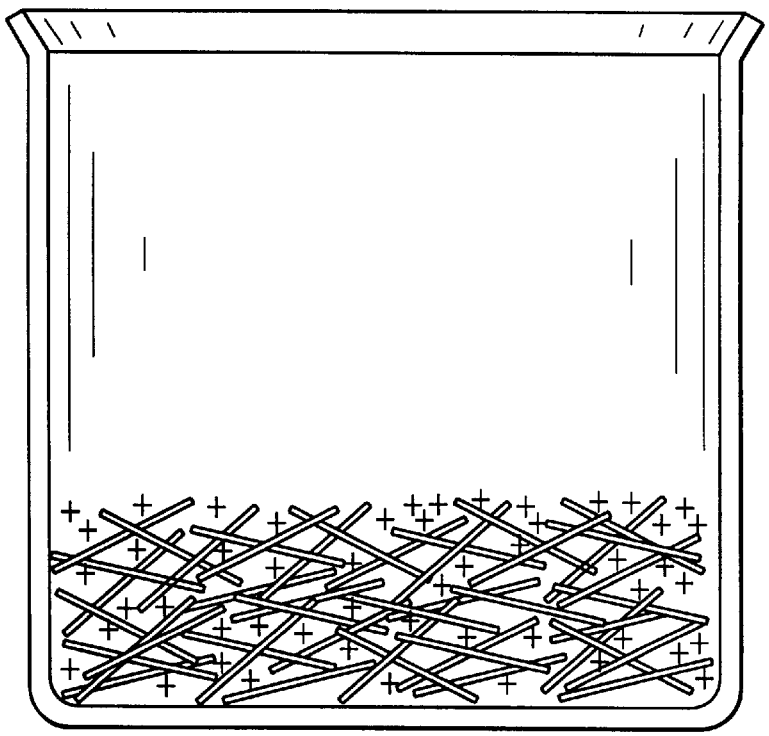
FIG. 1 is a schematic representation of the ingredients before forming flowable, compactible micro-particulates.

The present invention is a method of making chewable comestible units which disintegrate quickly in the mouth of the consumer and the units made therewith. The units produced in accordance with the present invention are soft and easily chewed. They disintegrate nearly instantaneously, i.e., within seconds, in the mouth. However, these units, which can be tablets, are capable of being manufactured so that they can be handled for packaging and distribution without deterioration of the integrity of the comestible units.

The first step of the method is to mix shearform matrix and an additive, such as an active ingredient. "Shearform matrix" in the present invention means a matrix or floss produced by subjecting a feedstock which contains a carrier material to flash flow processing.

Flash flow processing can be accomplished several ways. Flash-heat and flash-shear are two processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. The force necessary to separate and discharge flowable feedstock is centrifugal force produced by the spinning head.

"Flash heat" describes a process in which a feedstock is subjected to temperature, thermogradients, flow, flow rates and other forces of the type produced in certain types of machines One preferred apparatus for implementing a flash heat process is a "cotton candy" fabricating type of machine. Another is set forth in U.S. Ser. No. 964,257, filed Sep. 30, 1992.

Any other apparatus or physical process which provides similar forces and temperature gradient conditions can also be used. Useful devices are discussed in the U.S. Ser. No. 08/854,344, filed May 12, 1997, incorporated herein by reference.

In the flash-shear process, a shearform matrix is formed by raising the temperature in the feedstock material which includes a non-solubilized carrier, such as a saccharide-based material, until the carrier undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid communication with the means for increasing the temperature and is arranged at a point to receive the feedstock while it is in internal flow condition. The ejector is preferably a nozzle which provides high pressure ejection of the feedstock material. See U.S. Pat. No. 5,380,473, which is incorporated herein by reference.

The feedstock for producing shearform matrix includes a carrier or bulk material. The carrier material can be selected from materials which are capable of undergoing both physical and/or chemical changes associated with flash-flow processing. Materials useful as matrices may be chosen from those carbohydrates which are capable of forming free-form agglomerates upon being processed.

Preferred carrier materials are chosen from such classes as sugars or sugar derivatives. "Sugars" are those substances which are based on simple crystalline mono- and di-saccharide structures, i.e., based on $C_5$ and $C_6$ sugar structures. "Sugars" include simple sugars, e.g., glucose, sucrose, maltose, lactose, arabinose, xylose, ribose, fructose, mannose, pentose, galactose sorbose, dextrose, and sugar alcohols, e.g., sorbitol, xylitol, mannitol, pentatol, maltitol, isomalt, sucralose and mixtures of any of these.

Preferred combinations of sugars include the sugars above used in combination with other mono-, di-, tri-, and polysaccharides in amounts up to 50% of the total amount, preferably up to 30%, and most preferably up to 20%.

A shearform product is used in the technique of the present invention to obtain the new sugar product. A shearform sugar product is a substantially amorphous sugar which results from subjecting sugar to heat and shear sufficient to transform crystalline (usually granulated) sugar to amorphous sugar without the use of a solution. Thus, in the sense of the present invention, a shearfo:rm sugar product is characterized as a sugar product resulting from a non-solubilized sugar. It is the starting material for forming the unique crystalline product of the present invention.

Other carrier materials can be used, but preferably in combination with sugar—not as a total replacement. Maltodextrins are an example of other carrier materials. Maltodextrins include those mixtures of carbohydrates resulting from hydrolysis of a saccharide feedstock which are described as solids having a DE of up to and including 65.

The feedstock can also include maltooligo-saccharides produced by selective hydrolysis of cornstarch followed by removal of high and low molecular weight compounds. The general description of malto-oligosaccharides as contemplated herein is set forth in U.S. Pat. No. 5,387,431.

Polydextrose is also contemplated for use in combination with sugar in the carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of U.S. Pat. No. 5,279,849.

Polydextrose may be used as both a carrier and a crystallization/binding promoter.

"Initiating crystallization" in the present invention means to induce crystallization. Shearform matrix used in the present invention contains a substantial amount of amorphous sugar. Crystallization can be initiated several ways. For example, crystallization promoters can be included in the feedstock used to make the shearform matrix. Crystallization promoters include surface active agents such as Tweens™, Spans™, and polydextrose, and mixtures thereof. Crystallization can also be initiated by adding a crystallization agent to the matrix before or after combining with an additive. Therefore, initiating crystallization in the present invention can occur before or after combining with the additive.

"Combining" an additive with shearform matrix to form flowable, compactible micro-particulates means to add and mix an additive before or after initiating crystallization to form a medium which consists of micro-particulates. Micro-particulates are discreet entities which appear to "roll" readily or "flow" in response to force of gravity and/or agitation. On a macroscopic scale micro-particulates appear as a flowable mass or medium. Consequently, the medium can be easily used in tableting machinery without clogging and/or creation of undue dust in the ambient atmosphere.

The shearform matrix of the present invention is retrieved from processing, and generally "chopped" before combining with the additives. The additives can be any ingredient or ingredients, preferably active ingredients, needed to supply the comestible unit with required characteristics. Preferably, the primary additives include one or more medicinal substances.

Medicinal substances and other active ingredients which can be used in the present invention are varied. A non-limiting list of such substances is as follows: mineral supplements, vitamins, antacids, analgesics, anti-inflammatory substances, gastrointestinal agents, and mixtures thereof.

Preferred active ingredients are antacids. Antacid products can be prepared using calcium carbonate alone or in combination with magnesium hydroxide, and/or aluminum hydroxide and other antacid materials listed below. Another group of preferred actives uses combinations of calcium carbonate and/or another antacid with one or more $H_2$-antagonists as anti-ulcerative agents. Useful $H_2$-antagonists include: cimetidine, famatidine, omeprazole, and ranitidine and mixtures.

Vitamins such as Vitamin D can also be included in antacid-containing dosages.

Another group of especially preferred active ingredients include multi-vitamin preparations. One or more vitamins selected from the group consisting of Vitamins A, B1, B2, B6, B12, C, D, E, niacin and folic acid may be chosen. Especially desirable is a combination of one or more of the foregoing vitamins in an amount corresponding to a percentage of the U.S. Recommended Daily Allowance (RDA) for each vitamin, e.g. within the range of 0–100% or more. Along with vitamins, additional nutrients could also be included, especially those with desirable nutraceutical benefits. Contemplated are myriad botanical and herbal substances, including St. Johns wort, ginseng, ginkoba and other derivatives of plants, including bark, stems, flowers, leaves, roots and the like. Any of the foregoing vitamins and/or nutrients may be present in encapsulated form, using oleaginous materials and techniques available to those skilled in the art.

It is contemplated that active agent(s) and optional crystallization/binding promoter(s) are ingredients in the formulations from which the matrices are made.

The invention also includes a composition for delivering an active ingredient wherein the active ingredient is incorporated in a molded saccharide-based crystalline structure, which may have a bi-dimensionally stabilized crystalline sugar. The sugar is produced by forming a sugar crystalline frame from an outer portion of an amorphous shearform sugar mass, and subsequently converting the remaining portion of the mass to a substantially completely crystalline structure. The product is preferably monodispersed and is also preferably microcrystalline. For definitions of "monodispersed" and "microcrystalline," as well as definitions relating to other aspects of the present invention, reference is made to U.S. Pat. No. 5,597,416, which is incorporated herein by reference. The shearform mass can also include an additive which is co-crystallized in a crystalline product. The amorphous shearform mass is substantially rod-shaped, and has two dimensions lying in a cross-sectional plane of the rod. The single dimension extends along a linear axis of the rod. Preferably, the monodispersed structurally stabilized cross-section does not exceed 50 $\mu$m, and preferably does not exceed 10 $\mu$m.

Other ingredients which may be included are fragrances, dyes, sweeteners both artificial and natural, and other additives.

For example, fillers may be used to increase the bulk of the tablet. Some of the commonly used fillers are calcium sulfate, both di- and tribasic, starch, calcium carbonate, microcrystalline cellulose, modified starches, lactose, sucrose, mannitol, and sorbitol.

Other materials which can be incorporated into the feedstock to enhance the shearform matrix include flavors and sweeteners (other than the carrier itself).

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., beta-citral (lemon, lime) decanal (orange, lemon), aldehyde C-8 (citrus fruits), aldehyde C-9 (citrus fruits), adlehyde C-12 (citrus fruits), tolyl aldehyde (cherry, almond), 2,6-dimethyloctanal (green fruit), and 2-dodecenal (citrus, mandarin), mixtures thereof and the like.

The sweeteners may be chosen from the following non-limiting list: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as suralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Yet a further embodiment of the present invention includes the use of an effervescent disintegration agent. Its action can aid in the masking of objectionable taste of active ingredients such as antacids, vitamins, and/or minerals, etc. It is generally believed that the positive organoleptic sensation achieved by the effervescent action in the mouth, as well as the texture, speed and sensation of disintegration agents assist in masking undesirable flavor notes in the mouth.

In preferred embodiments of the present invention, the effervescent disintegration agent may include at least one acid selected from the group consisting of citric acid, tartaric acid, malic acid, fumaric acid, adipic acid, succinic acid, acid anhydrides and acid salts and mixtures thereof, and at least one base selected from the group consisting of carbonate salts, bicarbonate salts and mixtures thereof.

Also as previously mentioned, the ingredients of the effervescent agent can be included in one of at least three different ways. The first method includes incorporating the entire effervescent agent in the feedstock which is used to form the shearform product. The second manner of incorporating an effervescent disintegrating agent is to include the entire agent as an additive which is mixed with shearform matrix after it is formed. The third method contemplates incorporating one portion of the disintegrating agent in the shearform matrix and another portion of the disintegrating agent as an additive after formation of the shearform matrix material. The artisan will determine the best way to preserve the agent for its disintegrative and effervescent properties upon ingestion by the host.

The shearform matrix used in the inventive process must be uncured before it is molded. "Uncured" means amorphous or having a degree of amorphousness which enables the formation of a dosage unit upon curing. "Curing" means transforming the matrix from amorphous to crystalline while being sufficiently bound to produce a stable structure.

Curing can be enhanced by crystallization modifiers. Crystallization modifiers can be added to the feedstock before flash flow processing, such modifiers include, but are not limited to, surfactants (Spans™ and Tweens™), dextrose, polyethylene glycol (PEG), polypropylene glycol (PPG), etc. These modifiers generally provide controlled acceleration of crystallization while the matrix is bound.

Crystallization modifiers enhance the formation of a crystalline frame and the conversion of the remaining mass. "Enhancement" as used herein principally means acceleration of the process. "Enhancement" also includes contribution to the strength of the crystalline structure, and predictability of results. Other benefits, such as reduced-size product, can be achieved by use of crystallization modifiers.

Crystallization modifiers, which are preferably added to sugars before they are processed to amorphous shearform mass (or are optionally coated on the sugar), are used to affect the rate of crystallization. Water itself is a crystallization modifier, and is preferably included in the amorphous shearform sugar mass in an amount of between about 0 to about 2.0%. Materials found to be most effective as crystallization modifiers are surfactants having a hydrophilic to lipid balance (HLB) of six or greater, i.e., they have the same degree of hydrophilicity as surfactants characterized by degree of HLB. Such materials include, but are not limited to anionic, cationic and zwitterionic surfactants as well as neutral materials which have an HLB of six or greater. Preferred modifiers are hydrophilic materials having polyethylene oxide linkages. Also, preferred materials have a molecular weight of at least 200 and preferably at least 400.

Lecithin is one surface active agent for use in the present invention. Lecithin can be included in the feedstock in an amount of from about 0.25 to about 2.00% by weight. Other surface active agents include, but are not limited to, the Spans™ and Tweens™ which are commercially available from ICI Americas Inc. Carbowax™ is yet another crystallization modifier which is very useful in the pre sent invention. Preferably, Tweens™ or combinations of surface active agents are used to achieve the desired HLB.

One or more fillers may be used to increase the bulk of the tablet. Some of the commonly used fillers are calcium sulfate, both di- and tri basic, starch, calcium carbonate, microcrystalline cellulose, modified starches, lactose, sucrose, mannitol, and sorbitol.

Other ingredients include one or more binders which contribute to the ease of formation and general quality of the tablet. Binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Lubricants are also useful in tableting formulations. Lubricants can include, but are not limited to, one or more of the following: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

Furthermore, one or more dispersion enhancers can be used to enhance the breakability of the compressed tablet in an aqueous environment. The dispersants can include starch, alginic acid, polyvinylpyrrolidones, guar gum, partially hydrolyzed guar gum, kaolin, bentonite, purified wood cellulose, sodium starch glycolate, isoamorphous silicate, and microcrystalline cellulose as high HLB emulsifier surfactants. The product Benefiber, which is a partially hydrolyzed guar gum, is highly desirable for use in a chewable multi-vitamin composition. It is believed that this product may act as an adjuvant to those materials which break apart and disintegrate the tablet in the mouth.

In view of the ease with which the product of the present invention disintegrates, those skilled in the art may find little need for disintegrants. However, in at least one embodiment comprising a multi-vitamin formulation, certain disintegrants may be especially efficacious in assisting in dissolution of the final tablet in the mouth. Croscarmellose sodium, marketed under the trade name Ac-Di-Sol, is an example of one such suitable disintegrant.

Absorbents may also be utilized in the tablet preparations of the invention. These may be particularly desirable in the heretofore described multi-vitamin formulation in which highly water soluble vitamins are utilized. The absorbents act to prevent moisture from ruining the integrity of the overall composition, since unregulated moisture contributes to the dissolution of water-soluble actives contained therein. Maltodextrin may be especially preferred for its absorbency characteristics, as well as for its glidant properties.

Emulsifiers may also be utilized in the compositions of the invention to produce a highly consistent product, especially in those formulations wherein both water-soluble and non-soluble components are utilized. Mono- and diglycerides may be especially preferred, for example, those marketed under the brand names Myvatex and Myacet, as well as DurEm. Oleaginous substances such as food oils like Medium Chain Triglycerides (MCT) and Stearine D 17 (partially hydrogenated soybean oil) may also be desirable.

The combination of shearform matrix and the additive must be provided as Favorable, compactible micro-particulates. The micro-particulates include the ingredients of the mixture, but are relatively low density. The micro-particulates can then be compacted under relatively high compaction force to form a low density dosage unit having high structural integrity, strength and excellent appearance.

Micro-particulates are preferably formed by combining the mixture with at least one crystallization/binding promoter such as ethanol (preferably 200 proof), polyvinylpyrrolidone, or a combination thereof, as well as other agents which enhance the formation of micro-particulates, e.g., surface active agents, without increasing the density of the mixture. Ethanol is used in amounts of about 0.1 to about 5.0%, preferably about 4.0% or less, based on the total weight of the floss formulation. After ethanol contact, the floss is treated to remove any excess ethanol and optionally milled or screened. Other suitable, non-aqueous crystallization/binding promoters may also be used, in addition to or in lieu of any of the foregoing.

In some cases, a low compression force is used. Tablets made using the invention can have low densities and can be easily disintegrated.

"Compacting" in the present invention means to shape into a comestible unit, e.g., a tablet, at a pressure which need not be as great as normal tableting pressure.

As a result of the present invention, a quickly dispersable comestible unit can be manufactured for shipment and sales to consumers. Such manufacturing can proceed on a continuous basis. Since the agglomerate can be compacted with low to moderate compaction forces, a unit can be formed which is durable and can withstand the handling associated with packaging and distribution.

When chewable tablets are made, they are compressed to hardnesses of about 3 to about 15 SCU's, preferably about 4 to 6 SCU's. Thicknesses of about 0.25 to about 0.3 inches are typical.

Other ingredients can also be used in the present invention either during the mixing stage, during the agglomeration stage, or after the agglomeration stage. Such ingredients include glidants which adhere to the cohesive materials and enhance flow properties. Glidants which can be used include one or more of: starch, talc, magnesium and calcium stearate, zinc stearate, dibasic calcium phosphate, magnesium carbonate, magnesium oxide, calcium silicate, silica arogels, and the like.

Also color additives can be used in preparing tablets. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

The present invention is particularly useful for preparing antacid tablets. Antacids are conveniently provided in a chewable tablet form to provide a convenient method of delivering antacid to the consumer. The chewable form provides an advantage in that the tablet is broken up into granules during chewing and mixed with saliva before swallowing. This creates a suspension.

One of the disadvantages of current antacid tablets is that the mass of ingredients residing in the mouth during and after chewing have objectionable texture and taste. The present invention overcomes these disadvantages because of the rapid disintegration which occurs in the mouth. The objectionable texture and taste of disagreeable ingredients are reduced because the residence time in the mouth is substantially reduced.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts. Mixtures can be used.

Other highly desirable preparations include a chewable multi-vitamin formulation.

Figure 2:
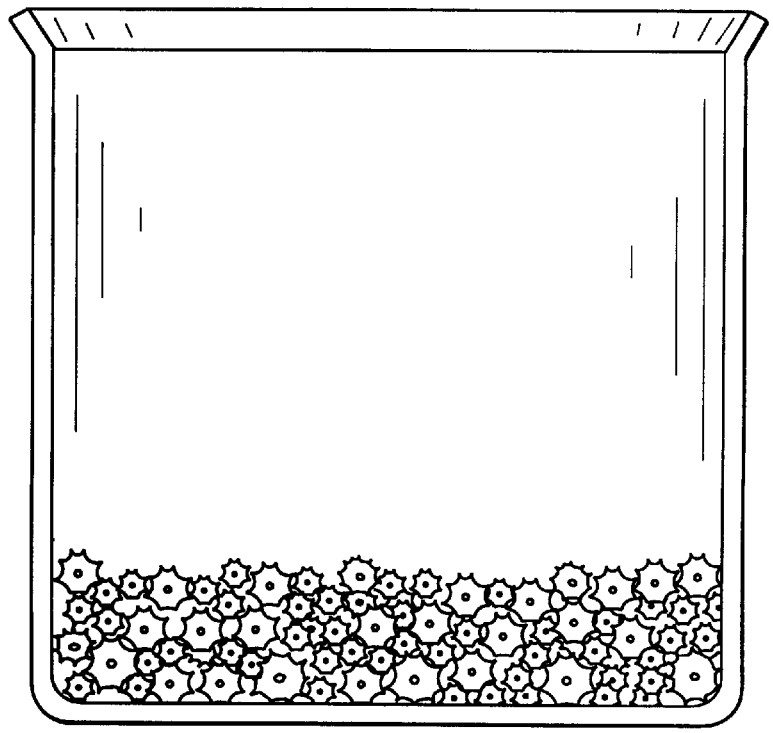
FIG. 2 is a schematic representation of micro-particulates formed from the mixture shown in FIG. 1.
Figure 3:
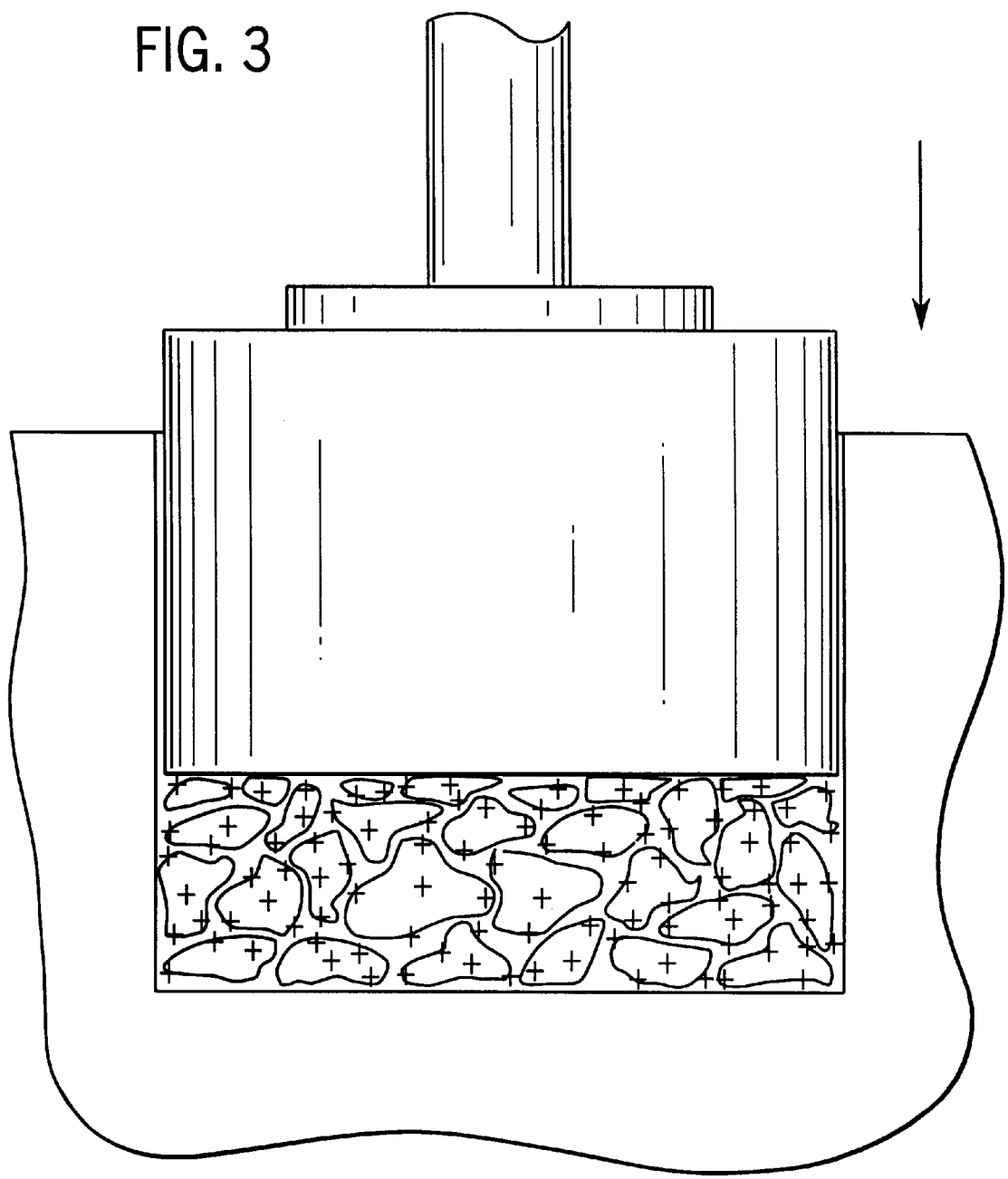
FIG. 3 is a schematic representation of compacting micro-particulates into a comestible unit in accordance with the invention.

Referring to FIGS. 1–3, the process of the present invention is described in greater detail. In FIG. 1, a combination of shearform matrix in the form of chopped floss material is depicted in mixture with a representative of an additive, i.e., +'s. An antacid agent or one or more vitamins is a preferred additive, +. In FIG. 1, the combination is shown as floss and additive particles indiscriminately mixed one with another. There is no fixed relationship between the particles in the mixture. Crystallization of the floss is initiated either before or after the combination with an additive is formed.

In FIG. 2, the combination is shown as flowable, compactible micro-particulates. The micro-particulates shown in FIG. 2 are represented by collections of shearform matrix with the additive fixed therein and thereon. The transformation is enhanced when the combination shown in FIG. 1 is subjected to a crystallization/binding promoter such as ethanol, polyvinylpyrrolidone, or a combination thereof. Other crystallization/binding promoters may be used to form the micro-particulates.

The micro-particulates form a medium which is flowable. Therefore, the medium is easily fed to dye cavities in tableting apparatus without clogging moveable parts, and the incidence of dust is reduced.

FIG. 3 is a schematic representation of the performance of the micro-particulates during actual compression. The micro-particulates are schematically represented under compaction force. They deform, but their density is not increased. Basically, the spaces between micro-particulates are reduced or virtually eliminated by agglomeration, but the micro-particulates themselves retain their low density. Additive particles are retained in and on the surface of the agglomerates.

Micro-particulates retain their individual integrity and lines of disintegration throughout the resulting unit. Moreover, since the mass can be subjected to relatively high-pressure-compaction (or compression) the surface of the resulting dosage unit is smooth, and the strength of the tablet is relatively high. The resulting units can be easily handled without deterioration of the surface appearance or destruction of the comestible units.

During formation of the micro-particulates the material preferably contains up to about 5% water, and most preferably up to about 1% water. The water can be provided by water contained in the ingredients such as that carried in the sugars or binders. Water can also be provided in small amounts in the alcohol, such as in 200 proof alcohol which absorbs moisture rapidly and generally contains small amounts of moisture, e.g., up to 1% by weight. Moisture can also be provided by ambient surroundings such as the humidity in the air.

EXAMPLES

ANTACID EXAMPLE

Shearform matrixes were prepared for use in the process of the present invention. The matrixes were prepared by subjecting combinations of carrier material to flash flow processing in a cotton candy type apparatus. The combination included the saccharide-based carrier material sucrose, as well as other carriers, and surfactants such as Tween™ 80, which is supplied by ICI, and lecithin. The isomalt used herein is commonly available as Palatinit™ brand isomalt. The blends were provided according to the formulae set forth below in the Shearform Matrix Table.

| SHEARFORM MATRIX TABLE AMOUNT (PERCENT) IN EACH MATRIX (M) | | |
|---|---|---|
| Ingredient | M1 | M2 |
| Sucrose (granules) | 66.5 | 66.5 |
| Mannitol (powdered) | 33.0 | 16.5 |
| Dextrose | — | 16.5 |
| Sorbitol | — | — |
| Surfactant | 0.5 | 0.5 |
| Isomalt | — | — |
| Maltitol | — | — |
| Polyglycerol esters | — | — |

The matrix recovered from each of the blends set forth above was a light colored floss, e.g., substantially white. Each matrix was then chopped for mixing with an additive, e.g., an antacid combination. The examples set forth hereinbelow refer to the matrices recovered from each of the blends above as M1 and M2.

ANTACID EXAMPLE I

The first antacid example was mixed in accordance with the formula set forth below in Antacid Table I.

| ANTACID TABLE I | |
|---|---|
| Ingredient | Percentage |
| Antacid Agent (CaCO$_3$) | 36.55% |
| M1 | 58.63% |
| Flavoring | 0.35% |
| Vegetable Oil Flow Agent | 0.50% |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
| | 100.00% |

The ingredients were combined by mixing to provide a mixture such as that shown in FIG. 1.

After the mixture was formed, ethanol (200 proof) was added and flowable compatible micro-particulates were formed. (About 4.0% of ethanol based on the weight of the mixture was used). The schematic representation of such agglomerates are shown in FIG. 2. After an agglomerate consistency was achieved, tablets were formed by compressing under a composition force of about 6 SCU. The weight of each tablet was about 1.500 grams. The tablets so formed had an excellent appearance, and disintegrated immediately in the mouth of the consumer. The release capabilities of the calcium from the dosage unit has been set forth below in the Calcium Release Table. As can be seen from the release capabilities, not only is the dosage unit an excellent source of antacid agent, but can also be classified as a source of calcium for purposes of nutrition. Therefore, the dosage unit can be characterized as a nutritional calcium supplement.

ANTACID EXAMPLE II

A second example was prepared using the mixture set forth below in Antacid Table II.

ANTACID TABLE II

| Ingredient | Percentage |
| --- | --- |
| Antacid Agent (CaCO₃) | 36.55% |
| M2 | 58.86% |
| Peppermint Flavoring (Peppermint Oil) | 0.12% |
| Vegetable Oil Flow Agent | 0.50% |
| Syloid 244 | 1.00% |
| Cab-O-Sil | 0.40% |
| Starch | 2.00% |
| High Intensity Sweetener (Aspartame) | 0.07% |
| Lubricant (Mg Stearate) | 0.50% |
|  | 100.00% |

The above ingredients were mixed together and then subjected to agglomerating in the presence of ethanol (200 proof). About 4% of ethanol based on the weight of the mixture was used. Flowable, compactible micro-particulate were formed.

The resulting agglomerate was directed to tableting press and compressed at a compression force of about 6 SCU. The resulting tablets were smooth and had a high quality appearance. Furthermore, the product disintegrated immediately in the mouth of the consumer. Tests were also conducted on two of the samples to determine the release characteristics of the calcium. The results of the test are shown in the Release Table as tests results IIa and IIb.

ANTACID EXAMPLE III

Another example of an antacid dosage unit was prepared in accordance with the mixture set forth in Antacid Table III.

ANTACID TABLE III

| Ingredient | Percentage |
| --- | --- |
| Antacid Agent (CaCO₃) | 36.550% |
| M2 | 58.630% |
| Flavoring | 0.350% |
| Vegetable Oil Flow Agent | 0.500% |
| Syloid 244 | 1.000% |
| Cab-O-Sil | 0.400% |
| Starch | 2.000% |
| High Intensity Sweetener (Aspartame) | 0.070% |
| Lubricant (Mg Stearate) | 0.500% |
|  | 100.000% |

The ingredients set forth above were thoroughly mixed and flowable, compactible micro-particulates were formed. The agglomerates were formed in the presence of ethanol added in an amount sufficient to form the micro-particulate consistency (about 4% by weight of the total mixture). The ethanol was mixed thoroughly with the ingredients and the agglomeration formed.

The micro-particulate medium was then directed to a tablet forming press wherein tablets were prepared using a compaction pressure of about 6 SCU. The resulting tablets were at a high quality appearance, and were able to disintegrate immediately in the oral cavity.

Furthermore, the tablets prepared in accordance with this example were subjected to analysis for calcium release and the results have been set forth in the Calcium Release Table hereinbelow.

CALCIUM RELEASE CHARACTERISTICS

An assay was conducted in order to determine the calcium release characteristics of the samples prepared as set forth above. The calcium release characteristics were prepared in accordance with the protocol set forth in the United States Pharmacopeia.

Several tablets were weighed and powdered, and the weight of each of the samples tested had a dosage amount of 550 mg. This powder was introduced to water to which 10 mm. of 1 N HCl had been added. This was boiled for 30 minutes, allowed to cool, and then transferred to a 100 mL volumetric flask with the aid of water. This was diluted with water to volume, mixed, and filtered. Twenty (20) mL. of the filtrate was transferred to a suitable container and diluted with water to 100 mL. Fifteen (15) mL. of 1 N NaOH was added along with 5 mL. of triethanolamine, and 100 mg. of hydroxy naphthol blue trituration, and titrated with 0.05 M of disodium ethylenediamine-tetraacetate VS until the solution is a deep blue color. Each mL. of 0.05 disodium ethylenediamine-tetraacetate is equivalent to 5.004 mg. of calcium carbonate (CaCO₃). The results of the assay have been set forth below in the Calcium Release Table.

CALCIUM RELEASE TABLE

| Sample | % Calcium Release |
| --- | --- |
| I. | 95.76 |
| IIa. | 95.21 |
| IIb. | 95.76 |
| III. | 95.48 |

As can be seen, the calcium released at 30 minutes was excellent on all the samples prepared in accordance with the present invention.

ANTACID EXAMPLE IV

Chewable, fast dissolving tablets containing calcium carbonate were made as follows. The floss referred to in section I was used in both tablets.

The following example illustrates the preparation of chewable antacid tables.

| I. Floss (Matrix) Formulation | |
| --- | --- |
| Sucrose | 58.5% |
| Mannitol | 23% |
| Sorbitol | 15% |
| Polydextrose | 3% |
| Tween 80 | 0.5% |

The sucrose and Tween 80 were blended in a AFM or Hobart 160 quart planetary mixer at 70 to 120 rpm for 5 to 10 minutes. The mannitol, sorbitol, and polydextrose were added and blended for additional 15 to 20 minutes. The blend was then subjected to shearform process at 60 Hz and 180–185° C. temperature using the 5" crown head described in U.S. Ser. No. 08/854,344, filed May 12, 1997. The floss manufactured was chopped by the turning blades rotating at 60 Hz and collected by the cyclone. The chopped floss was treated with ethanol (200 Proof, 4% by weight of the formulation) by spraying the ethanol on the floss in a planetary mixer and mixing it for 10 minutes. The floss was placed in Gruenberg Oven trays and dried at 35–40° C. for 60 minutes in the oven. The floss was then milled/sieved through a 20 mesh screen using a Quadro Comil.

II. Tablet Formulations

A. Cherry Flavor

| | |
|---|---|
| Calcium Carbonate USP | 36.07% |
| Floss | 55.51% |
| Mannitol USP | 5.00% |
| Artificial Cherry Flavor | 0.10% |
| Cherry Cream | 0.25% |
| Aspartame | 0.07% |
| Syloid 244FP | 1.25% |
| Cab-O-Sil | 0.50% |
| D&C Red #27 Aluminum Lake | 0.25% |
| Magnesium Stearate | 1.00% |

The calcium carbonate was blended and sieved in a AFM or Hobart 106 quart planetary mixer at 70 to 120 rpm for 5 to 10 minutes. The flavors, mannitol, color, and sweeteners were blended for 5 minutes in a separate container and added to the planetary mixer. The flow agents were added and blended for additional 10 minutes. The magnesium stearate was added and blended for additional 5 minutes. The blend was compressed on a rotary tablet press at 5 SCU hardness, 0.276 inch thickness, 1.525 g tablet weight, ⅝ inch dimple face round tooling. Using the same procedure used for the cherry flavor, tablets containing peppermint flavors were prepared from the following formulation.

B. Peppermint Flavor

| | |
|---|---|
| Calcium Carbonate USP | 36.07% |
| Floss | 55.65% |
| Mannitol USP | 5.00% |
| Betanat Natural Peppermint Flavor | 0.15% |
| Peppermint Oil of Kennewick | 0.05% |
| Natural Whipped Cream | 0.20% |
| Magnasweet 100 | 0.03% |
| Aspartame | 0.10% |
| Syloid 244FP | 1.25% |
| Cab-O-Sil | 0.50% |
| Magnesium Stearate | 1.00% |

The peppermint tablets were pressed to 5 SCU hardness, 0.276 inch thickness, and 1.525 g tablet weight using ⅝ inch dimple face round tooling.

VITAMIN FORMULATION EXAMPLE V

I. Floss (Matrix) Formulation

| | |
|---|---|
| Sucrose | 99.5% |
| MCT Oil | 0.25% |
| Myvacet 707 | 0.25% |

The floss matrix was prepared in a substantially similar manner to Example IV above. The floss was then utilized to prepare a chewable, multi-vitamin supplement as follows:

| | |
|---|---|
| Floss | 40% |
| Vitamins* | 14% |
| Sweeteners/Flavors** | 1–2% |
| Sorbitol 60W | 30% |
| Maltodextrin (Maltrin M100) | 2.0% |
| Disintegrant | 4.0% |
| Disintegrant Adjuvant | 2.0% |
| Myvatex MS | 3.5% |
| MCT Oil | 0.5% |
| Myvatex TL | 0.75% |
| Syloid 244 | 0.5% |

*included Vitamins A, B1, B2, B6, B12, folic acid, Vitamin C, D3, E and niacin. B vitamins and folic acid encapsulated using 4:1 ratio of DurEm 117, Myvacet 707 and Stearine D17 to vitamins.
**included aspartame, citric acid and other natural/artificial flavors.
Ingredients were mixed in a Hobart mixer, and compressed into tablets using a Rimek tablet press. Each tablet weighed approximately 2.0 grams. Each tablet contained 100% of the RDA of the stated vitamins, and was quick-dissolving and delicious.

While there had been described what are presently believed to be the preferred embodiments of the present invention, those skilled in the art will appreciate that other and further embodiments can be made without departing from the spirit of the invention and it is intended to include all such further modifications and changes as come within the true scope of the claims as set forth herein.

What is claimed is:

1. A method of preparing a quick dissolve comestible unit comprising:
    a) initiating crystallization of shearform matrix particles comprising at least one member selected from the group consisting of monosaccharides, disaccharides, trisaccharides, polysaccharides, malto-oligosaccharides and sugar alcohols;
    b) before or after initiating crystallization combining an additive with said shearform matrix to form flowable, compactible micro-particulates, said additive being at least one member selected from the group consisting of vitamins, mineral supplements and nutraceuticals; and
    c) compacting said micro-particulates resulting from step "b", which includes at least partially crystallized shearform matrix, to form said comestible unit.

2. A method of preparing a chewable quick dissolve comestible unit comprising:
    a) initiating crystallization of shearform matrix particles by contacting them with a crystallization/binding promoter, said particles comprising at least one member selected from the group consisting of monosaccharides, disaccharides, trisaccharides, polysaccharides, malto-oligosaccharides and sugar alcohols;
    b) after initiating crystallization, combining at least one additive with said particles, said additive being selected from the group consisting of vitamins, mineral supplements and nutraceuticals; and
    c) compressing the product of step b) to form said comestible unit.

3. The method of claim 2 wherein the shearform matrix is a floss prepared from a composition comprising: about 99.5% sucrose, and wherein the remaining percentage comprises one or more oleaginous materials.

4. The method of claim 3 wherein the comestible unit is prepared from a formulation comprising one or more vitamins selected from the group consisting of vitamins A, B1, B2, B6, B12, folic acid, C, D3, E and niacin.

5. A composition for preparing a chewable quick dissolve comestible unit comprising:
    a) about 40–45% of a floss prepared from a composition comprising about 99.5% sucrose and one or more oleaginous materials; and
    b) one or more active ingredients, wherein the floss has been contacted with a crystallization/binding promoter.

6. The composition of claim 5 wherein said active ingredient includes at least one vitamin.

7. The composition of claim 6 wherein said active ingredient includes a multi-vitamin formulation.

8. The composition of claim 7 wherein said multi-vitamin formulation comprises at least one member selected from the group consisting of vitamins A, B1, B2, B6, B12, C, D, E, niacin and folic acid.

9. The composition of claim 8 wherein said multivitamin formulation is at least one anti-oxidant vitamin.

10. The composition of claim 9 wherein said anti-oxidant vitamin is selected from the group consisting of vitamins A, C and E.

11. A comestible unit comprising the composition of claim 7.

12. A comestible unit produced according to the process of claim 2.

13. A rapidly dissolving delivery system for oral administration of active substances comprising at least one member selected from the group consisting of emulsifiers, oleaginous substances, and absorbents.

14. The delivery system of claim 13, further comprising at least one member selected from the group consisting of disintegrants, glidants and disintegrant adjuvants.

15. The delivery system of claim 14, comprising a combination selected from the group consisting of mono and diglycerides, croscarmellose sodium, partially hydrolyzed guar gum and maltodextrin.

16. The delivery system of claim 15, further comprising at least one first member selected from the group consisting of vitamins, mineral supplements, nutraceutical and pharmaceutical active substances and at least one second member selected from the group consisting of monosaccharides, disaccharides, trisaccharides, polysaccharides, malto-oligosaccharides and sugar alcohols.

17. The delivery system of claim 16, wherein said first member and said second member comprise about 40 to 90% of said delivery system.

18. The composition of claim 5 wherein said active ingredient comprises calcium carbonate.

19. The composition of claim 13 wherein said delivery system further comprises calcium carbonate.

* * * * *